US012806029B2

(12) United States Patent
Kowalczyk et al.

(10) Patent No.: US 12,806,029 B2
(45) Date of Patent: Nov. 24, 2026

(54) TALUS FORMATION AND IMPLANTATION METHOD

(71) Applicant: PARAGON ADVANCED TECHNOLOGIES, INC., Englewood, CO (US)

(72) Inventors: Gregory J. Kowalczyk, Little Silver, NJ (US); Selene G. Parekh, Cary, NC (US); Luciano Bernardino Bertolotti, Buenos Aires (AR)

(73) Assignee: PARAGON ADVANCED TECHNOLOGIES, INC., Englewood, CO (US)

( * ) Notice: Subject to any disclaimer, the term of this patent is extended or adjusted under 35 U.S.C. 154(b) by 0 days.

(21) Appl. No.: 19/089,961

(22) Filed: Mar. 25, 2025

(65) Prior Publication Data

US 2025/0221826 A1 Jul. 10, 2025

Related U.S. Application Data

(63) Continuation of application No. 17/036,485, filed on Sep. 29, 2020, now Pat. No. 12,257,157.
(Continued)

(51) Int. Cl.
*B33Y 10/00* (2015.01)
*A61F 2/30* (2006.01)
(Continued)

(52) U.S. Cl.
CPC ........ *A61F 2/4202* (2013.01); *A61F 2/30942* (2013.01); *B29C 64/386* (2017.08);
(Continued)

(58) Field of Classification Search
CPC ....... A61F 2/3094; A61F 2/4202; B33Y 10/00
See application file for complete search history.

(56) References Cited

U.S. PATENT DOCUMENTS

| | | | |
|---|---|---|---|
| 3,839,742 | A | 10/1974 | Link |
| 7,736,381 | B2 | 6/2010 | Biedermann |

(Continued)

FOREIGN PATENT DOCUMENTS

| | | |
|---|---|---|
| GB | 2379185 | 3/2003 |
| WO | 2009076758 | 6/2009 |

(Continued)

OTHER PUBLICATIONS

Fang et al. Total talar replacement with a novel 3D printed modular prosthesis for tumors. Therapeutics and Clinical Risk Management. Vo. 14 pp. 1897-1905, 2018 (Year: 2018).*

(Continued)

*Primary Examiner* — Cachet I Proctor
(74) *Attorney, Agent, or Firm* — Heslin Rothenberg Farley & Mesiti P.C.

(57) ABSTRACT

A process for printing a talus implant comprising the steps of scanning a joint for a damaged talus, and scanning a contralateral joint for a healthy talus. Next, the process includes obtaining dimensions for a talus based upon an initial scan and then obtaining dimensions for a talus based upon the scan of the contralateral joint. Next the process includes inverting the dimensions of the talus in the contralateral joint and then comparing the dimensions of the calculated talus with a pre-set of dimensions in a database. Next the process includes exporting a set of dimensions to a printer to print a talus implant.

15 Claims, 11 Drawing Sheets

Related U.S. Application Data

(60) Provisional application No. 62/908,438, filed on Sep. 30, 2019.

(51) Int. Cl.

| | |
|---|---|
| ***A61F 2/42*** | (2006.01) |
| ***B29C 64/386*** | (2017.01) |
| ***B33Y 50/00*** | (2015.01) |
| ***B33Y 80/00*** | (2015.01) |
| ***G16H 30/40*** | (2018.01) |
| ***G16H 50/30*** | (2018.01) |
| ***G16H 50/50*** | (2018.01) |
| *B29L 31/00* | (2006.01) |

(52) U.S. Cl.

CPC ............... *B33Y 10/00* (2014.12); *B33Y 50/00* (2014.12); *B33Y 80/00* (2014.12); *G16H 30/40* (2018.01); *G16H 50/30* (2018.01); *G16H 50/50* (2018.01); *A61F 2002/30116* (2013.01); *A61F 2002/30322* (2013.01); *A61F 2002/30578* (2013.01); *A61F 2002/30878* (2013.01); *A61F 2002/30909* (2013.01); *A61F 2002/30952* (2013.01); *A61F 2002/30985* (2013.01); *A61F 2002/4207* (2013.01); *B29L 2031/7532* (2013.01)

(56) References Cited

U.S. PATENT DOCUMENTS

| | | | | | |
|---|---|---|---|---|---|
| 8,932,363 | B2 | | 1/2015 | Tsougarakis | |
| 9,186,154 | B2 | | 11/2015 | Li | |
| 10,688,726 | B2 | | 6/2020 | Shidid | |
| 10,912,652 | B2 | | 2/2021 | Fonte | |
| 10,952,865 | B2 | | 3/2021 | Leemrijse | |
| 2009/0149965 | A1 | * | 6/2009 | Quaid | A61B 17/1668 623/22.4 |
| 2011/0004317 | A1 | * | 1/2011 | Hacking | A61F 2/4261 600/416 |
| 2012/0239045 | A1 | * | 9/2012 | Li | A61B 17/157 606/88 |
| 2016/0331467 | A1 | | 11/2016 | Slamin | |
| 2017/0246004 | A1 | * | 8/2017 | Goldberg | A61F 2/4202 |
| 2017/0360488 | A1 | | 12/2017 | Kowalczyk | |
| 2019/0358046 | A1 | * | 11/2019 | Ehmke | A61F 2/4202 |

FOREIGN PATENT DOCUMENTS

| | | | | |
|---|---|---|---|---|
| WO | 2014036551 | | 3/2014 | |
| WO | WO-2014036551 A1 | * | 3/2014 | A61B 17/8897 |

OTHER PUBLICATIONS

Tracey et al. Total talar replacement with a novel 3D printed modular prosthesis for tumors. Sage Journals. vol. 12. Issue 1. pp. 39-48 (Year: 2018).*

Fang, Xiang, et al., "Total Talar Replacement with a Novel 3D Printed Modular Prosthesis for Tumors", Therapeutics and Clinical Risk Management, vol. 14, pp. 1897-1905, doi:10.2147/tcrm.s172442, Oct. 5, 2018.

Ruatti, Sebastien, et al., "Total talar prosthesis replacement after talar extrusion", The Journal of Foot and Ankle Surgery, 56.4, pp. 905-909, Jul. 2017.

Tracey et al., "Custom 3D-Printed Total Talar Prostheses Restore Normal Joint Anatomy Throughout the Hindfoot", Foot & Ankle Specialist, Vo. 2, No. 1, pp. 39-48, Mar. 2018.

Dhillon MS, Rana B, Patel S, Kumar P., "Management Options in Avascular Necrosis of Talus", Indian J Orthop., pp. 284-296, May-Jun. 2018.

* cited by examiner

FIG. 2A
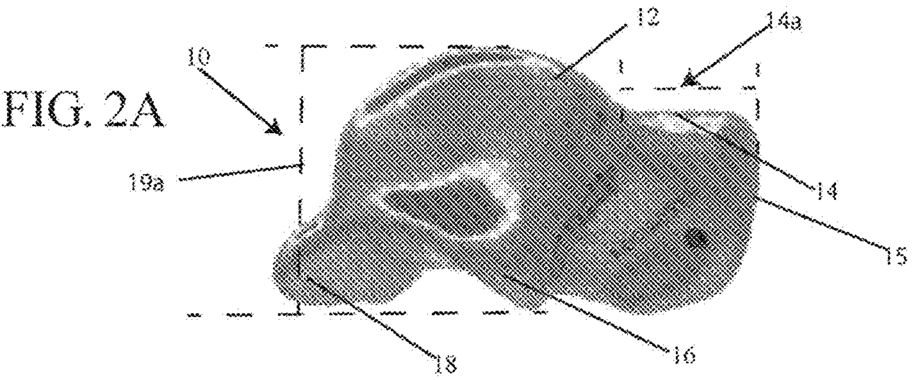
FIG. 2B
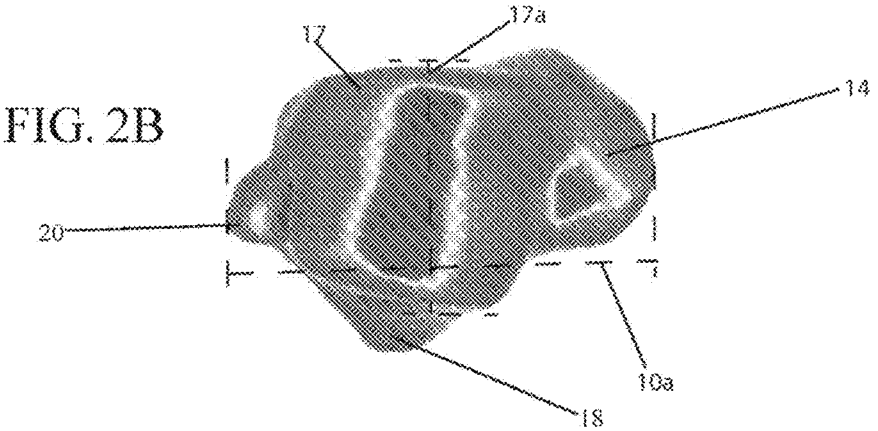
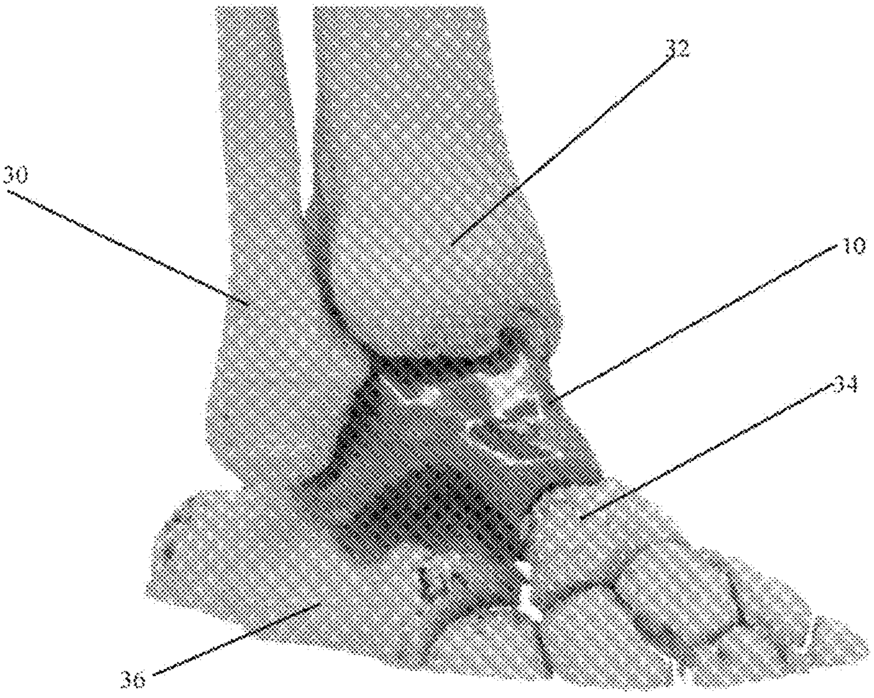
FIG. 2C

FIG. 6A
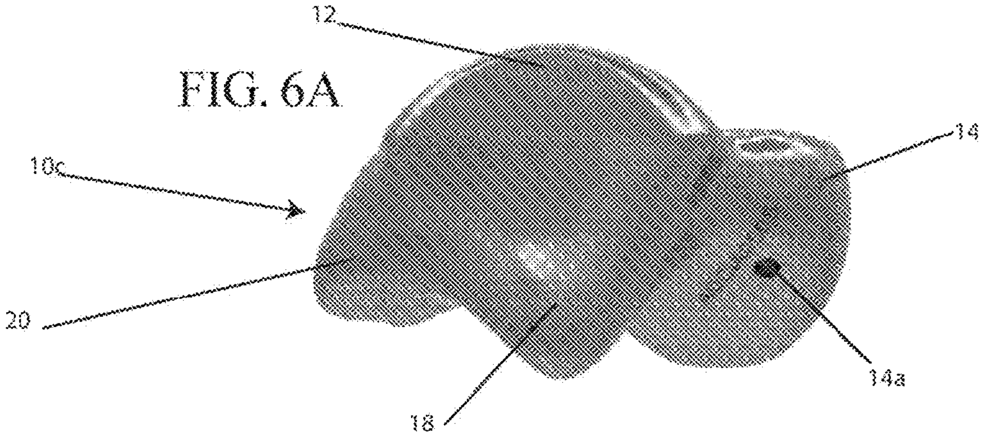
FIG. 6B
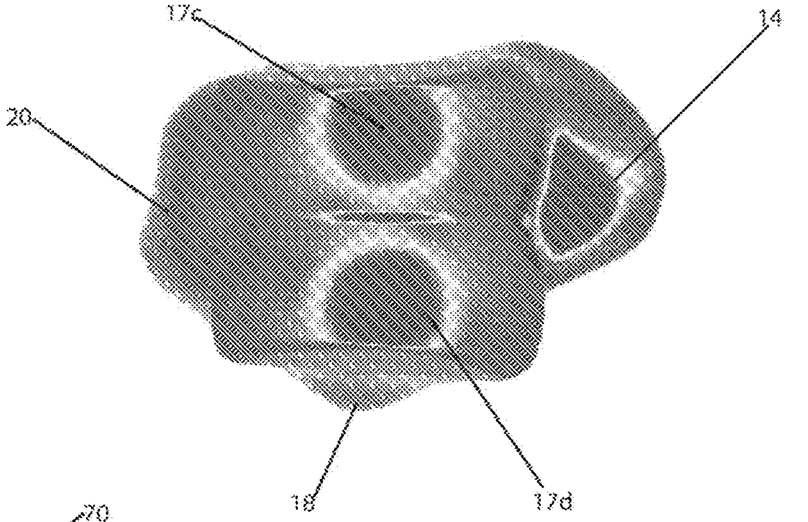
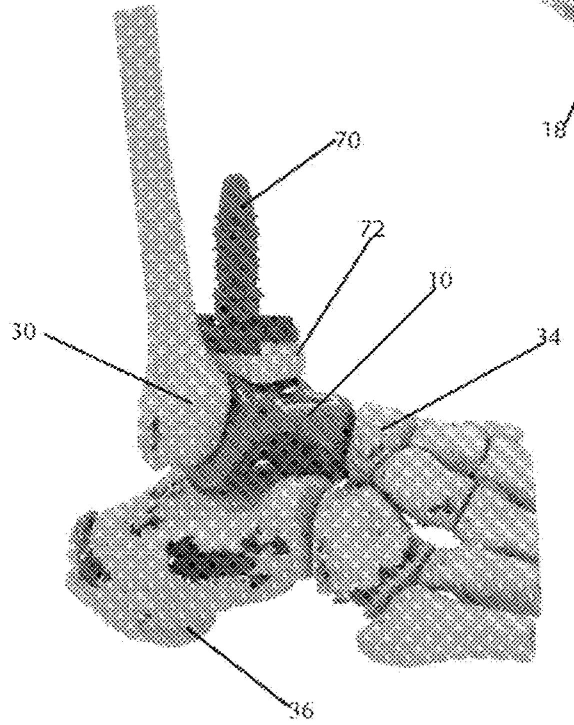
FIG. 6C

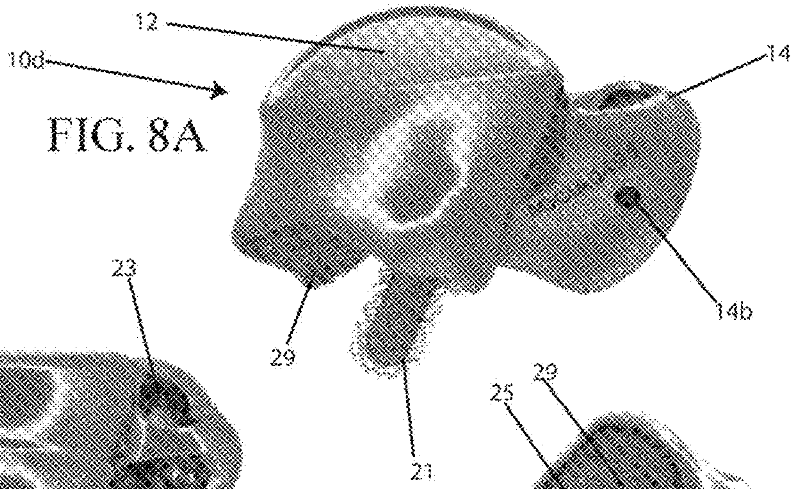
FIG. 8A
FIG. 8B
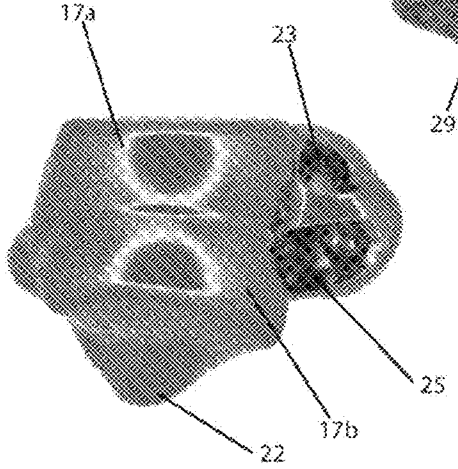
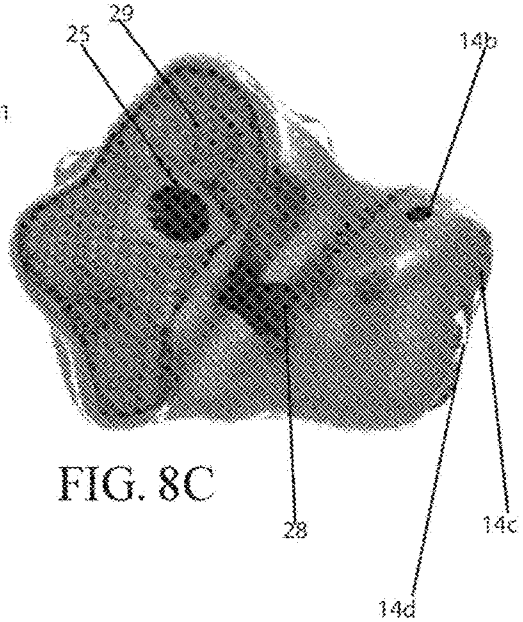
FIG. 8C
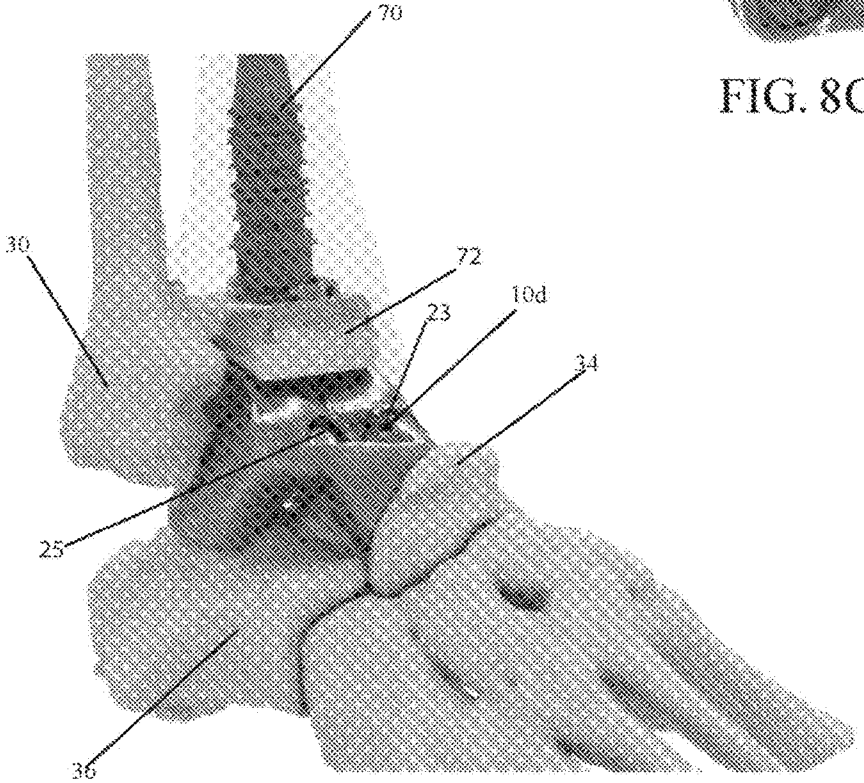
FIG. 8D

TALUS FORMATION AND IMPLANTATION METHOD

CROSS REFERENCE TO RELATED APPLICATIONS

This application is a continuation of U.S. application Ser. No. 17/036,485 filed on Sep. 30, 2019, which issued as U.S. Pat. No. 12,257,157 on Mar. 25, 2025, which claims priority to U.S. Provisional Application Ser. No. 62/908,438 filed on Sep. 30, 2019, the disclosures of which are hereby incorporated by reference in their entireties.

BACKGROUND

At least one embodiment of the invention relates to a talus implantation and formation method. A talus bone or ankle bone is one of a group of foot bones known as the tarsus. The tarsus forms the lower part of the ankle joint through its articulations. The talus bone can transmit the entire weight or a substantial portion of the weight of the body to the foot. The talus bone is extensively covered in cartilage. The talus forms part of the talocalcaneonavicular joint along with the calcaneus or heel bone and the navicular. The talus can comprise the following basic parts, the head, the neck and the body.

Talus injuries can be difficult to heal. For example, the talus bone lacks a good blood supply and as such those with a broken talus bone may not be able to walk for many months without crutches. Thus, many patients find a need for a talus implant.

The insertion of a talus implant can start with an incision to the ankle joint such that it involves exposure of the ankle joint and eventual movement or removal of obstruction of the extensor hallucis longus tendon, the anterior tibial artery, the extensor longus muscle. Once the talus bone that is injured is exposed it can be removed from the ankle joint. This talus can be held in place by the syndesmosis and anterior tibiofibular ligament as well as the anterior talofibular ligament and the superficial deltoid ligament. Once a talus bone is removed, a talus implant can be inserted into its place. However, since the talus bone can interact with other bones in different joints there is a need for a talus replacement and/or implant method and system so that a new talus can be accurately created and then implanted in a patient for future use.

SUMMARY

In at least one embodiment of the invention, there is a process for creating a talus and then implanting the created talus into a patient. For example, the process starts with a first step of scanning a joint. Once the joint is scanned such as using a cat scan, a first generic image of a talus is created. This image is a 3-D image that is created from the scan of the talus, wherein the following dimensions are calculated-talar height, talar arc length and talar width. Next the system can determine the alignment dimensions. The alignment dimensions can include the tibiotalar, the talar tilt angle, the talar declination angle, Boehler's angle, and Meary's angle. In addition, the patient's demographic information is input into the system as well. Once the talus has been removed it is examined for damage along with the surrounding area to determine possible interactions for the talus future talus implant. The possible interactions include interactions with neighboring bones as well as the surrounding joint. Depending on the level of damage to the talus the contralateral hindfoot can also be scanned. From this scan the system can invert the dimensions or take the mirror image of the dimensions to then fine tune or create the image of the talus. In at least one embodiment, based upon the above dimensions, the mirror image dimensions and optionally the patient's demographic information, can be used to determine which type of talus to use. For example, this information can be matched with an existing database of previous patients with respect to the dimensions of the prospective talus. Next, the implant is printed. Once the implant is printed it is coated. The coating can be of any suitable coating but in at least one embodiment is a nickel-plated cobalt coating. One process for creating the plating or coating could be through EBM or electron beam melting. Next, the implant is polished. Once the implant has been polished, it is reinserted into the user's body and then the implant can be evaluated for existing interactions. If there are any unexpected interactions, then the talus or the surrounding joint around the talus can be modified to better fit the talus inside of the user's body. Based upon the different interactions with other bones with the talus multiple different paths could be formed.

For example, a first path can be formed where there is no arthritis between the adjacent bones. Thus, a talus can be formed and polished and coated with no further modifications being necessary. Along a second path, there can be discovered arthritis in the subtalar joint wherein a lattice is formed on a bottom surface of the talus. Alternatively, a third path can be formed wherein there is extensive arthritis around a substantial portion of the joints affecting the talus such that there are multiple faces having a lattice structure. In addition, there can be a fourth path for the creation of the talus wherein there is discovery of arthritis of the navicular joint which includes exposure of a face having a lattice to the navicular. A fifth path can include any combination of the above paths to form a hybrid structure of a talus having multiple faces which contain a lattice structure.

Ultimately there can be many different paths for constructing or 3D printing a talus implant or a talus implant with a partial or substantial reconstruction of an ankle joint.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views:

FIG. 2A is a side view of a printed talus according to the first path;

FIG. 2B is a top view of a printed talus of FIG. 2A;

FIG. 2C is a view of the talus implanted into the ankle joint;

FIG. 6A is a side view of the talus printed using the flow chart of FIG. 5;

FIG. 6B is a top view of the talus shown in FIG. 6A;

FIG. 6C is a side view of the talus implant including a tibia implant inserted into the ankle joint;

FIG. 8A is a side view of the talus created using the flow chart of FIG. 7;

FIG. 8B is a top view of the talus of FIG. 8A;

FIG. 8C is a bottom view of the talus;

FIG. 8D is a side view of the talus;

DETAILED DESCRIPTION

Figure 1:
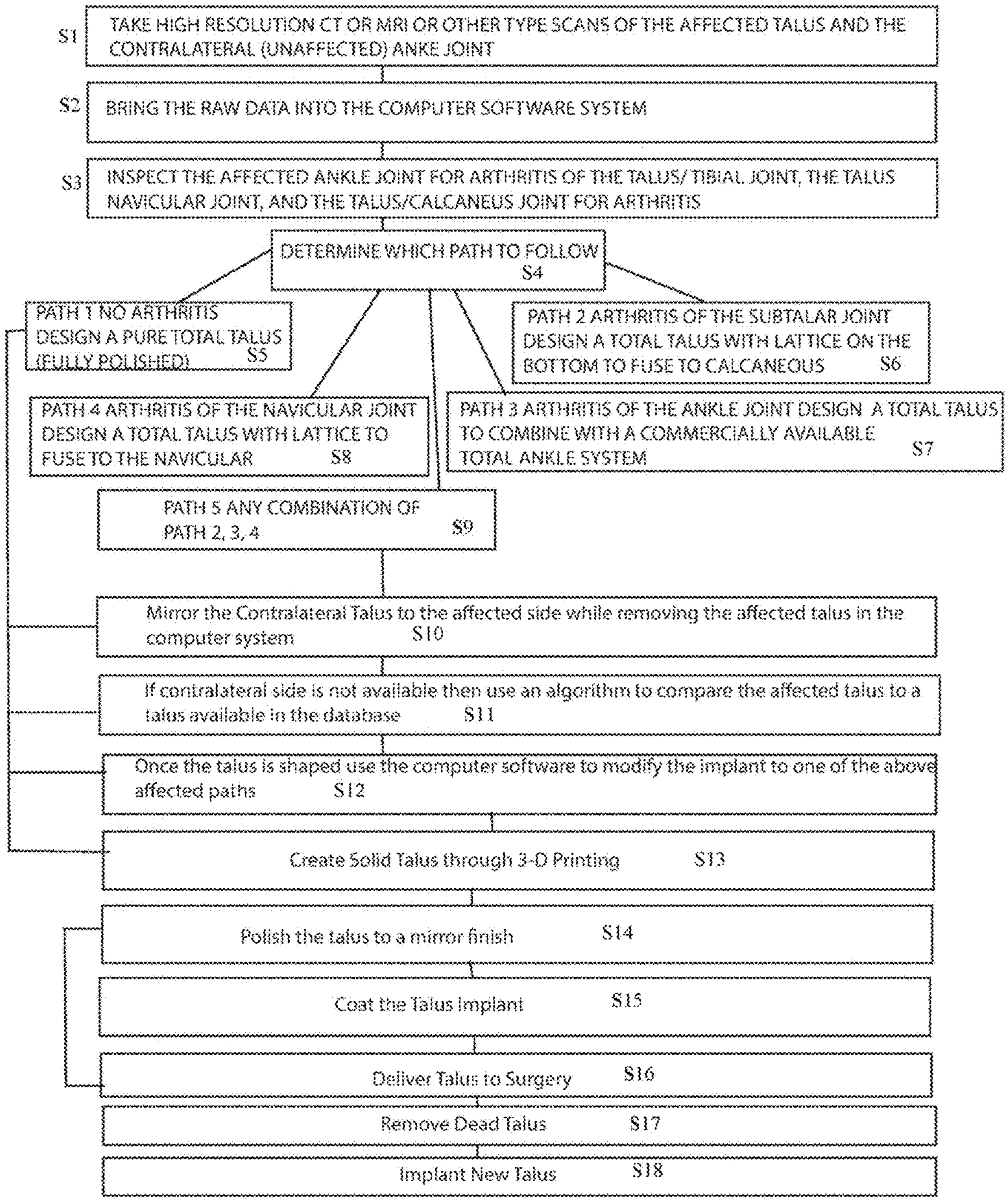
FIG. 1 is a schematic flow chart of the first main process for creating a talus implant.

FIG. 1 is a flow chart for the process for creating at least one talus implant and then implanting the talus into a patient's joint. For example, the process starts with step S1 wherein a high resolution CT or MRI is taken of an affected patient's talus as well as the contralateral unaffected ankle joint in step S1. Next, in step S2, the raw data is imported into the system such as into a computer 100, which could be used to represent any one of first initial computer 140, second computer 150, or application server 130. Upon viewing the scans the scans can be inspected so that the affected ankle joint is inspected for arthritis of the talus or tibial joint, the talus and the navicular joint and the talus and the calcaneus joint. Upon inspection of the joint, a particular path can be selected in step S4. For example, if the patient has no visible or apparent arthritis outside of the failure of the initial talus bone, then a single total talus replacement can be fabricated in for example step S5. This path would be considered the first path to select. Other paths are also possible such as path 2 wherein there is recognized arthritis of the subtalar joint wherein there can be a design of the total talus with a lattice on the bottom to fuse to the calcaneus bone in step S6. Alternatively, in step S7, path 3 can comprise recognizing that there is arthritis of the ankle joint, wherein there is a total talus to combine with a commercially available total ankle system. Alternatively, there can be in path 4 a recognition of arthritis of the navicular joint wherein there is a design of a total talus with a lattice to fuse to the navicular bone in step S8. Alternatively, in step S9 there can be some combination of the paths 1, 2, 3, and 4 in a new path 5 wherein there is some combination of arthritis to the ankle joint.

Once the path has been selected the contralateral talus (disposed on the opposite unaffected leg) that has been scanned can be mirrored in image and dimensions to the affected side. Once the talus has been mirrored, the scanned talus from the affected side can be removed or separately stored so as to not affect the properly mirrored version in step S10. However, if the contralateral side is not available then the system can use an algorithm to compare the affected talus to the talus available in a pre-set database. The pre-set database can be in the form of a database stored in database server 120 and reviewed by a processor such as microprocessor 102 in application server 130. The algorithm can include examining the talus based upon dimensions such as an the overall length of the talus (see dimension 10*a* in FIG. 2B), the overall width of the talus such as dimension 17*a* in FIG. 2B, the height of the talus 19*a* or the length of the neck of the talus 14*a* as well.

Next, the process proceeds to step S12 wherein the talus is shaped and sized using the dimensions calculated by either the mirror image of the contralateral talus or via the dimensions of the talus in the database to create a new talus for printing and production. This step involves first creating the base talus and then modifying the talus to fit one of the above affected paths. For example, any one of the paths such as path 1 listed in step S5, path 2 listed in step S6, path 3 listed in step S7 or path 8 listed in step S8.

Next, in step S13 the system creates a solid talus by printing the talus via 3D printing. An example of a talus that is created is shown in FIGS. 2A-2B with the talus being implanted as shown in FIG. 2C.

Next, in step S14 the talus can be polished to a mirror finish. Next, in step S15 as an option, the talus can also be coated with a coating. The coating can be of any suitable coating but in at least one embodiment is a nickel-plated cobalt coating. Next, in step S16 the talus can be delivered to the surgery. The talus can be shipped as part of a kit which involves repair of other parts of the ankle joint, or alternatively, it can be shipped alone. Next, in step S17 the surgeon can remove the dead talus, and then implant the new talus as shown in step S18. An example of the new talus being implanted is shown in FIG. 2C.

FIG. 2A is a side view of a talus implant 10 which includes a base or body section 12 a neck section 14 and a head section 15. In addition, there are shown the medial process 16 the lateral process 18 and the posterior process 20 as well. On top of the body section 12 is an articular surface 17 for the distal tibia dome. The talus can also have pre-set dimensions wherein there is a pre-set dimension for the neck of the talus as dimension 14*a*. In addition, there is a height of a talus 19*a* as well as a width of the talus 17*a* and the overall length of the talus 10*a* can also be calculated. These dimensions can be taken from an existing talus that is affected and should be removed, or alternatively these dimensions can be taken from a contralateral talus and then derived by taking a mirror image of the talus to create the dimensions of a talus implant. Alternatively, the dimensions of the affected or compromised talus if not entirely destroyed could be compared to dimensions on an existing database to determine from storage in a database the appropriate dimensions to construct or print a talus implant.

FIG. 2C shows the talus 10 that is implanted into an ankle joint. This talus 10 is shown positioned between a tibia 32, a fibula 30, a calcaneus 36 and a navicular 34. The talus implant is therefore created to fit inside of this ankle joint so that the different joints between the talus 10 and the surrounding bones are created once the talus is implanted into the joint. The above FIGS. 2A-2C show the design and implantation of the talus implant into a joint that is not affected by arthritis. However, after scanning a joint, different types of a talus implant can be created.

Figure 3:
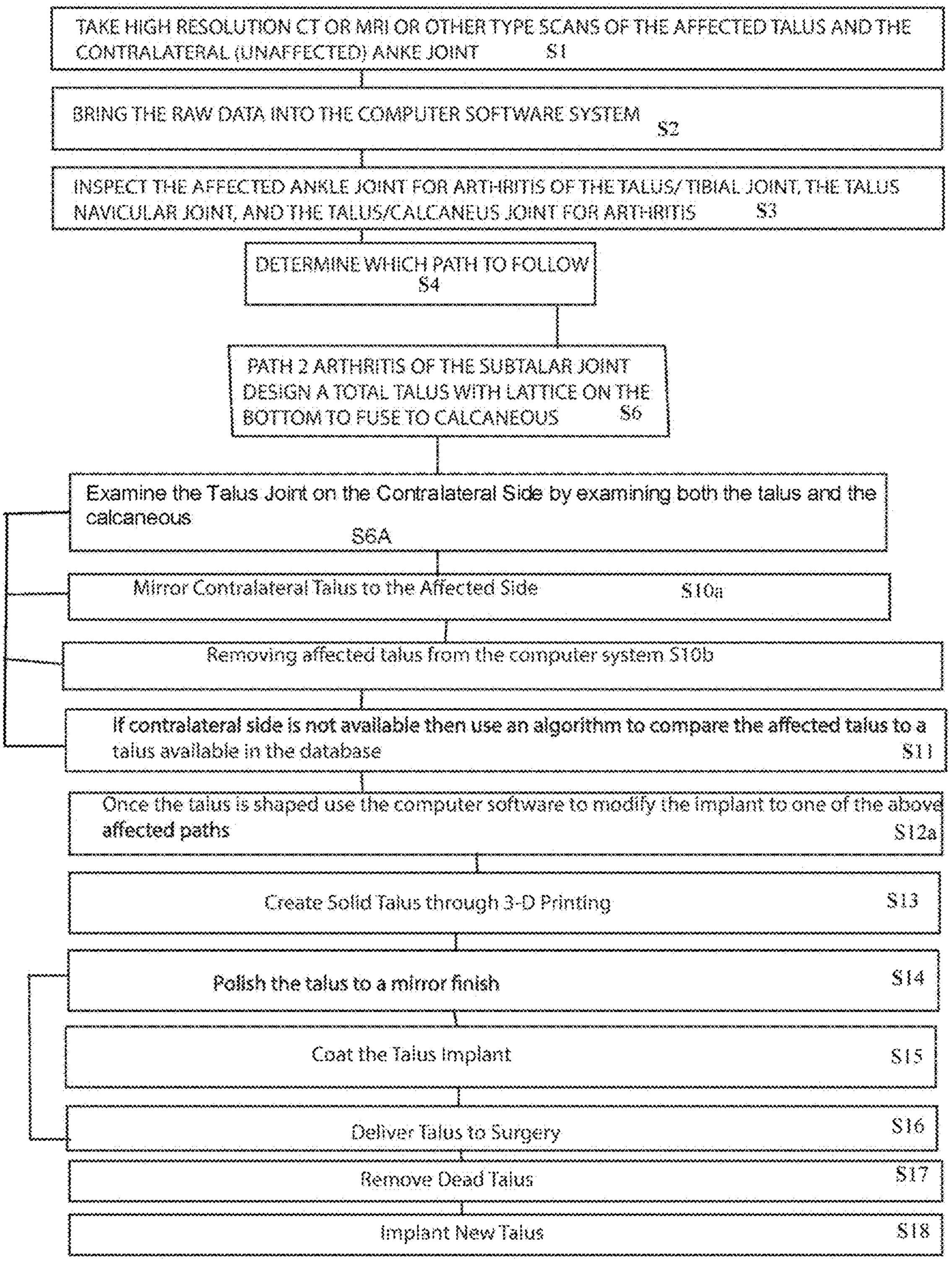
FIG. 3 is a flow chart for the second path outlined in FIG. 1.

For example, FIG. 3 shows an alternative process for creating a talus implant. With this process steps S1-S4 are substantially the same. However if during examination it is decided that path 2 is the correct path, then there is a design so that it handles the arthritis of the subtalar joint so that a talus is designed with a lattice on the bottom to fuse to the calcaneus in step S6. Thus, in step S6*a* the ankle joint can be examined so that the talus such as talus 10*b* and the calcaneus such as the calcaneus 36 are examined for interaction. In addition, as described in FIG. 1 the contralateral talus is mirrored to the affected side and once the dimensions of the contralateral talus are taken in step S10*a*. Alternatively, since the contralateral talus does not have the specific interactions between the affected talus and the arthritic joint between the talus and the calcaneus, this step of removing the affected talus can be skipped in step S10*b*. If the contralateral side is not available, then an algorithm is used to compare the affected talus to the talus available in the database such as in database server 120 in step S11.

Figure 4A:
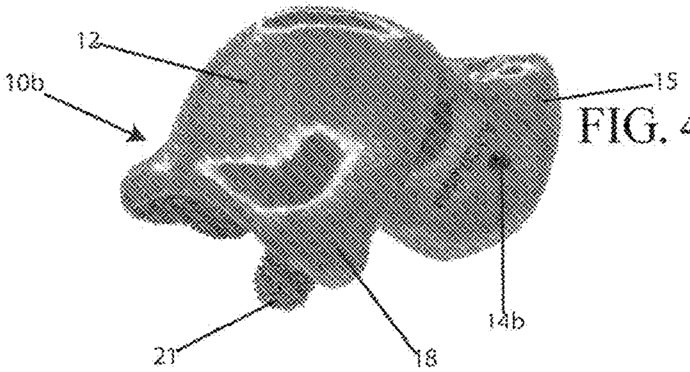
FIG. 4A is a side view of the talus created according to the second path.
Figure 4B:
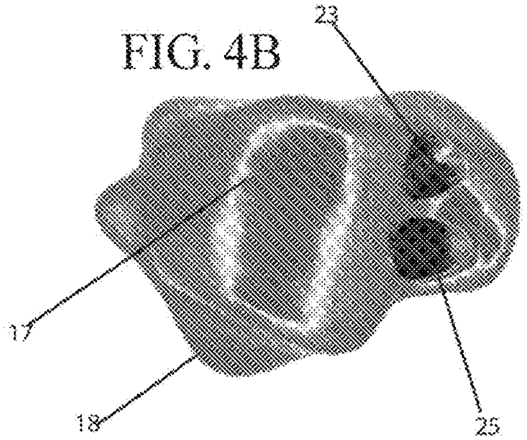
FIG. 4B is a top view of the talus according to the second path.
Figure 4C:
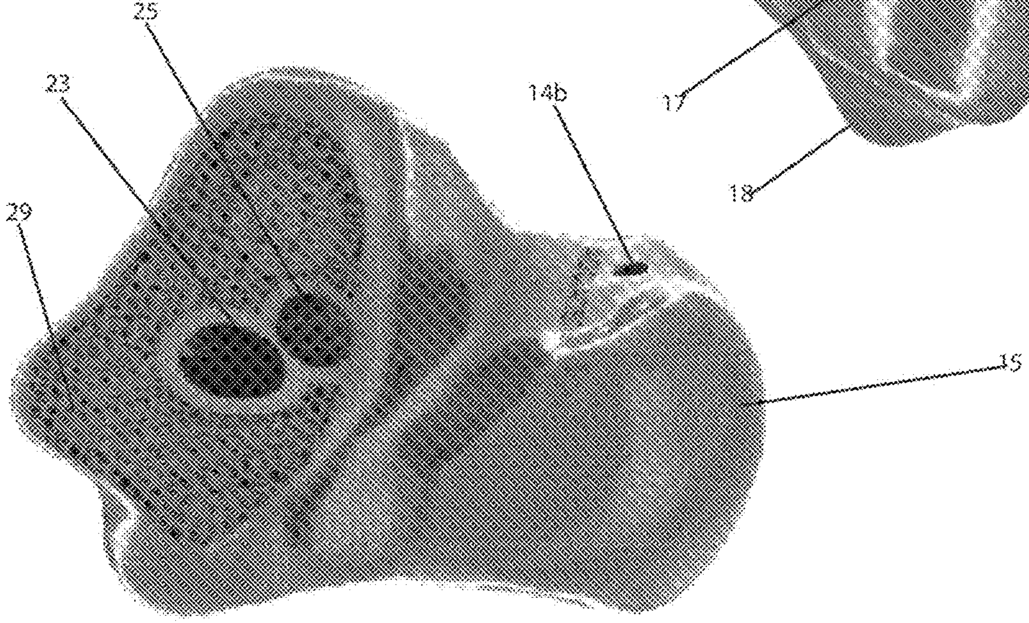
FIG. 4C is a bottom view of the talus.

Once the talus is shaped, the application server 130 can used computer software or an algorithm to modify the implant to the affected paths. This includes forming a lattice or mesh for creating interactions on a bottom surface of the talus as shown in FIGS. 4A and 4C which show both a mesh 29 and a post 21 disposed on the underside of the talus 10*b* as described in step s12*a*. Next, the application server 130 and/or processing computers 140 and/or 150 through an associated microprocessor such as microprocessor 102 can create the solid talus through 3-D printing in step S13. Next, the talus can optionally be polished to a mirror finish in step S14. However, since the bottom of the talus 10*b* is created with a roughened or lattice or mesh surface structure the bottom surface of the talus such as the mesh 29 is not polished. Next, in step S15 the talus is coated. Next in step S16 the talus is delivered to surgery wherein in step S17 the dead talus is removed and in step S18 the new talus is implanted.

FIG. 4A is a side view of the talus 10*b* which includes a base or body section 12, a neck 14 and a head 15. There is a lateral process 18 as well as an under mesh side 29 with an optional post 21. Post 21 extends down from the under mesh side of the talus. Drill holes 23 and 25 are shown extending through the talus, particularly through the neck of the talus and on to the underside of the talus. The mesh 29 can be formed in any suitable shape but in at least one embodiment it is formed as a lattice structure having repeating honeycomb patterns. These repeating honeycomb patterns are suitable for interactions with other adjacent bone structures. In at least one embodiment shown in FIG. 4A there is a post hole 14*b* in neck 14, and a head positioned adjacent to post hole 14*b*. There is also body 12 which extends down to lateral process 18. Disposed adjacent to lateral process 18 is a post 21. Post 21 is formed with a lattice structure as well. The post 21 is formed to interact with adjacent bone structure, such that there is inter-lattice bone growth to create a fusion between this structure and the adjacent bone structure. The post 21 is configured to create subtalar fusion to the calcaneus bone.

Figure 4D:
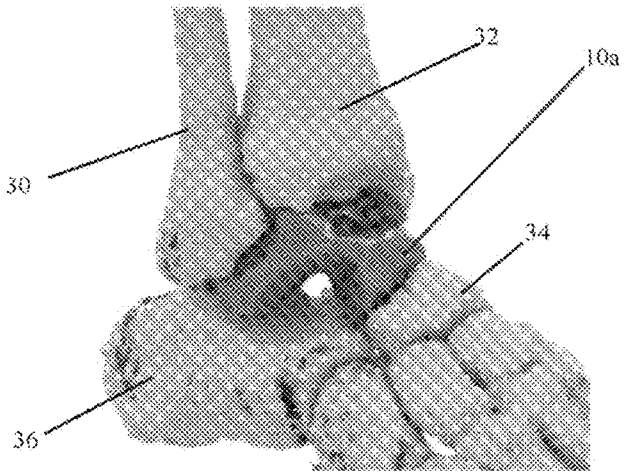
FIG. 4D is a side view of the talus implanted into the ankle joint.

FIG. 4D shows the view of the talus installed in an ankle joint. This ankle joint is formed by the fibula 30, the tibia 32, the calcaneus 36 and the navicular 34 all joining around the talus 10*a* to form the ankle joint.

Figure 5:
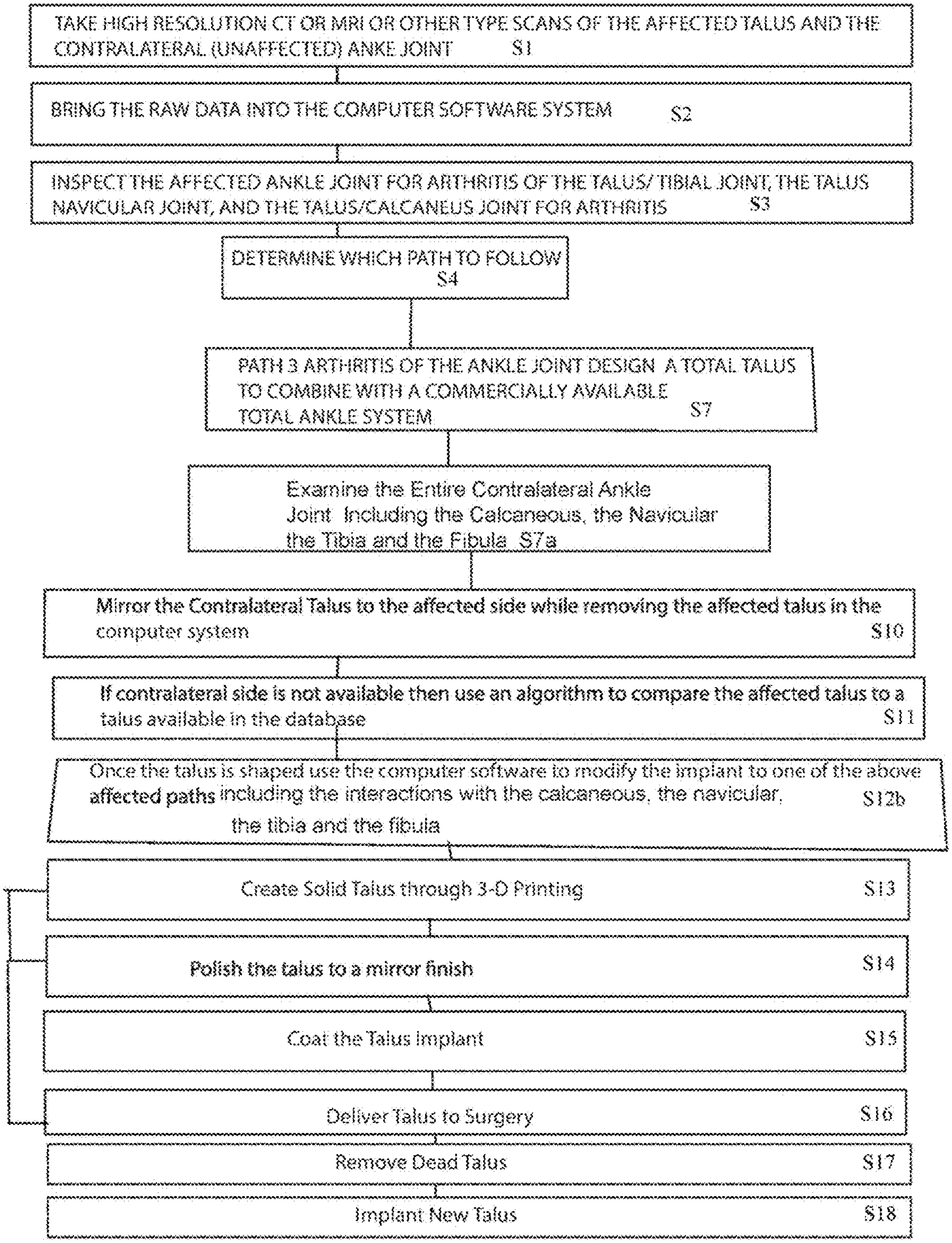
FIG. 5 is a flow chart for the third path for creating the talus.

FIG. 5 is a flow chart of the process for forming an implant based upon the third path outlined in FIG. 1. For example, with this process, there is the scanning of the affected area and the contralateral area in step S1. Next, the raw data is imported in step S2. Next, in step S3 the affected ankle joint is inspected for arthritis, wherein the area inspected includes the talus, the tibia, the fibula, the navicular joint, and the talus/calcaneus joint for arthritis. Next, in step S4 the practitioner can determine which path to follow. In at least one embodiment, such as in any one of the embodiments disclosed in FIGS. 1, 3, 5 and 7 the determination of which path to follow can be formed via a decision by a practitioner selecting the path or via an assistance from a program or algorithm determining that there is arthritis in the joint and then that algorithm determining via an application server such as application server 130 determining that there is arthritis in at least one joint. Next, in step S7 the system determines that there is arthritis in the ankle joint so that there is a total talus design to combine with a commercially available total ankle system. Since there is extensive arthritis to the joint, the system and/or practitioner can examine the entire contralateral ankle joint including the calcaneus, the navicular the tibia and the fibula in step S7*a*. Next, in step S10 the contralateral talus is mirrored to the talus on the affected side. If the sizing and shape of the contralateral talus appears to fit inside of the affected area, then the dimensions of the affected side talus are removed from use in the algorithm to determine the proper size and shape of the talus in step S10. Next, in step S11 if the contralateral side is not available then an algorithm is used to compare the dimensions of the affected talus to a talus available in the database. As described above, the algorithm includes taking the dimensions of the talus including the length of the talus, the width of the talus, the length of the neck of the talus, the height of the talus. In addition, some of the additional factors that can be used include the size, weight, bone structure, and gender of the patient to determine the proper sizing of a talus implant for the patient's affected joint.

Next, in step S12*b* once the talus is shaped, the system including the application server 130 can be used to determine the affected paths including the interactions with the calcaneus, the navicular, the tibia, and the fibula. Next, in step S13, the system can create the solid talus through 3-D printing of the talus. Next, in step S14, the talus can be selectively polished. Next, in step S15 the talus can be selectively coated. The coating as described above can be a nickel-plated cobalt coating. Next, in step S16, the talus can be delivered to surgery so that it is available for implant. In this case the talus can be delivered together with a total ankle replacement system. In step S17 the dead talus can be removed while in step S18 the new talus can be implanted.

FIGS. 6A-6C show the designs that can be implanted into an ankle joint. For example, with this design there is a talus 10*c* which has a body section 12. There is also shown a lateral process 18, a posterior process 20, along with a neck 14 and a post hole 14*b*. As shown in FIG. 6B there is a first articular surface 17*c* for the tibia, as well as a second articular surface 17*d* for the fibula. FIG. 6C shows another view which includes a partial ankle replacement, which includes a tibia post 70 which replaces an affected tibia. This tibia post 70 includes a tibia plate 72 for interaction with the talus implant 10*c*.

The talus implant is shown in FIG. 6C as being positioned adjacent to the fibula 30, the navicular 34 and the calcaneus 36. The tibia post 70 is configured to be screwed into an end of a tibia bone so as to replace a damaged end of a tibia bone.

Figure 7:
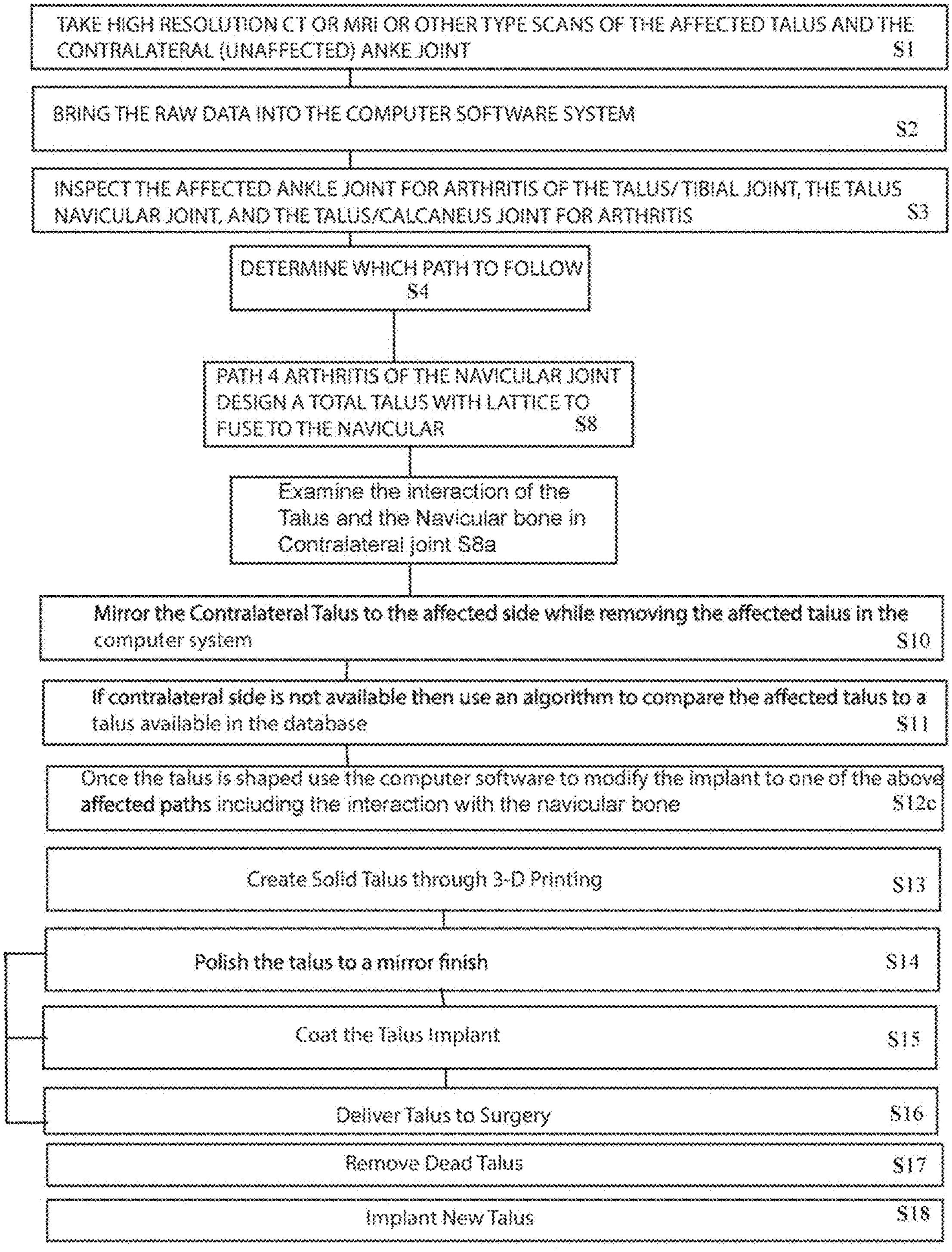
FIG. 7 is a flow chart of the fourth path for creating a talus.

FIG. 7 shows another version of the process which was outlined in FIGS. 1, 3, and 5. Steps 1-4 are the same as in the other flowcharts of FIGS. 1, 3, and 5. With step S8, the fourth path is chosen, wherein a practitioner or algorithm determines the fourth path for the creation of the talus with respect to an arthritic condition of the navicular joint. Thus, in step S3, the practitioner or system (algorithm on application server 130) can examine the interaction of the talus and the navicular bone in the affected area for arthritis. If there is discovered any form of arthritis in this affected area then the fourth path in step S8 is chosen. Along with the examination of the joint in the affected area, the contralateral joint is also examined such that the navicular bone, the talus bone and the interaction between the talus bone and the navicular bone is examined in step S8*a* to determine whether there is any arthritis in the affected joint. Next, in step S10 the contralateral talus is mirrored so that the proper dimensions of the talus can be created. If the size and shape of the talus is correctly mirrored and created, then the dimensions of the affected talus are removed from the calculation of the talus to be printed. If however, the contralateral side in step S11 is not available then the system such as application server 130 can use an algorithm to compare the affected talus to a talus available in a database. This calculation is based upon the perceived appropriate dimensions of a talus including its overall length, the length of the neck, its width and its height. Other variables such as the demographic information about the patient can also be used in this determination.

Once the talus is shaped, the system such as application server 130 can determine in step S12C whether to modify the implant to make the implant more receptable to interacting with a navicular bone positioned adjacent to the implant. The different calculations that can be performed to reshape the talus can be based upon the amount of affected area for interaction with the navicular bone, the shape of the adjacent navicular bone, the strength or mass or density of the adjacent navicular bone as well as the demographics of the patient (age, gender, weight, body mass etc). Next in step S13 a solid talus can be created through 3D printing. The talus bone can be created so that it has a mesh surface that interacts with an adjacent navicular bone as well as an adjacent calcaneus bone or an adjacent tibia or fibula bone as well.

Next, in step S14 the talus is polished to a mirror finish. Next, the talus is optionally coated in step S15. In step S16 the talus is delivered to surgery. During surgery in step S17, the talus is removed, while in step S18 the talus is implanted into the patient.

FIGS. 8A-8D show the different parts of the talus as it is created. For example, there is shown a talus 10*d* which has a mesh underside 29, a post 21 a neck 14, a post hole 14*b* shown in FIG. 8A which is a side view of the talus. The mesh, or lattice structure 29 has an uneven surface and which can extend beyond the outer frame such as body 12. This mesh or lattice structure is configured to create interstitial bone growth that leads to fusion to an adjacent bone such as an adjacent calcaneus bone. FIG. 8B is a top view of the talus which includes a first articular surface 17*c* for interaction with a tibia, and a second articular surface 17*d* for interaction with a fibula. Screw holes 23 and 25 are shown in the neck region 14 of the talus. There is also a lateral process 18 shown in FIG. 8B.

FIG. 8C shows a side view of the talus which shows the talus implant having a mesh face that therefrom. With this design, there is a screw hole 28, a post hole 14*b* and a mesh side face 29. The mesh side face 29 is made from a mesh or lattice structure.

With this design there is also an additional face 14*c* which is in place of the head 15. This additional face 14*c* has a mesh or lattice structure which can be in a honeycomb pattern and which in at least one embodiment extends beyond the outer fame and allows for interstitial bone growth that encourages meshing with an adjacent navicular bone. The openings of the honeycomb pattern can be the same in dimension or vary in their size such as be wider at the outer extremity while narrowing as it moves inward towards the center of the body. In addition, this face includes a screw hole 14*d*. Ultimately, this additional face 14*c* is configured to interact with the navicular such as navicular 34 and therefore form an interaction with navicular 34 so that the mesh or lattice structure can selectively bond to the navicular. With any one of the mesh or lattice structures present, a growth chemical, solution, or material can be injected into the lattice structure before implantation so that once the implant is inserted into the body, the lattice interacts with an adjacent bone to promote bone growth into the lattice.

FIG. 8D shows a side perspective view of the talus 10*c* being inserted into the ankle joint. In this view, there is a fibula 30, a tibia implant 70 and a tibia plate 72 shown positioned adjacent to the fibula 30. There is also shown the calcaneus 36, and the navicular 34 as well. In addition, in this view there are screw holes 23 and 25 which allow for the insertion of screws into the implant and for securing the implant into adjacent areas, particularly into the fibula.

Figure 9:
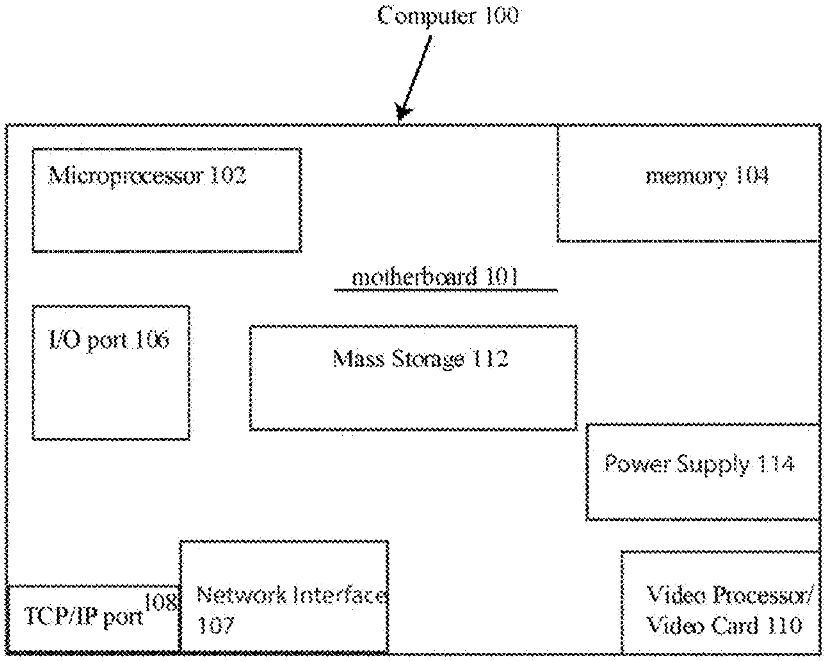
FIG. 9 is a schematic block diagram of a typical computer used in the process outlined in FIGS. 1, 3, 5 and 7.

FIG. 9 is a schematic block diagram of a computer which is used to process the information described above such as the images and dimensions of the existing talus, the mirror image talus and the three (3) dimensionally printed talus. For example, there is a computer 100 which includes a motherboard 101 and a microprocessor 102 which is coupled to the motherboard. In addition, there is a memory 104 coupled to the motherboard. The memory can be in the form of a RAM memory such as SRAM (Static Ram), DRAM (Dynamic Ram), SDRAM (Synchronous Dynamic Ram), DDR SDRAM (double data rate SDRAM). Any other type of suitable ram can also be used as well. The computer can also have input and output ports (I/O) ports 106 which can be in the form of serial, USB firewire or any other sort of input or output ports. A TCP/IP port 108 can also be used which is coupled to a network interface 107. A network interface can be in the form of a wireless or wired network interface wherein the network interface is associated with a MAC address as well as a TCP/IP identity on a network. In addition, coupled to the motherboard 101 is a video processor/video card 110 which is configured to read any input of video signals and/or process any input of video signals. A mass storage 112 is also coupled to the hard drive. The mass storage 112 can be in the form of a hard drive. Furthermore, there is a power supply 114 which is coupled to the motherboard 101 as well. This computer can be representative of any one of the computers shown in FIG. 10 such as any one of database server 120, application server 130, first initial processing computer 140, second initial processing computer 150.

Figure 10:
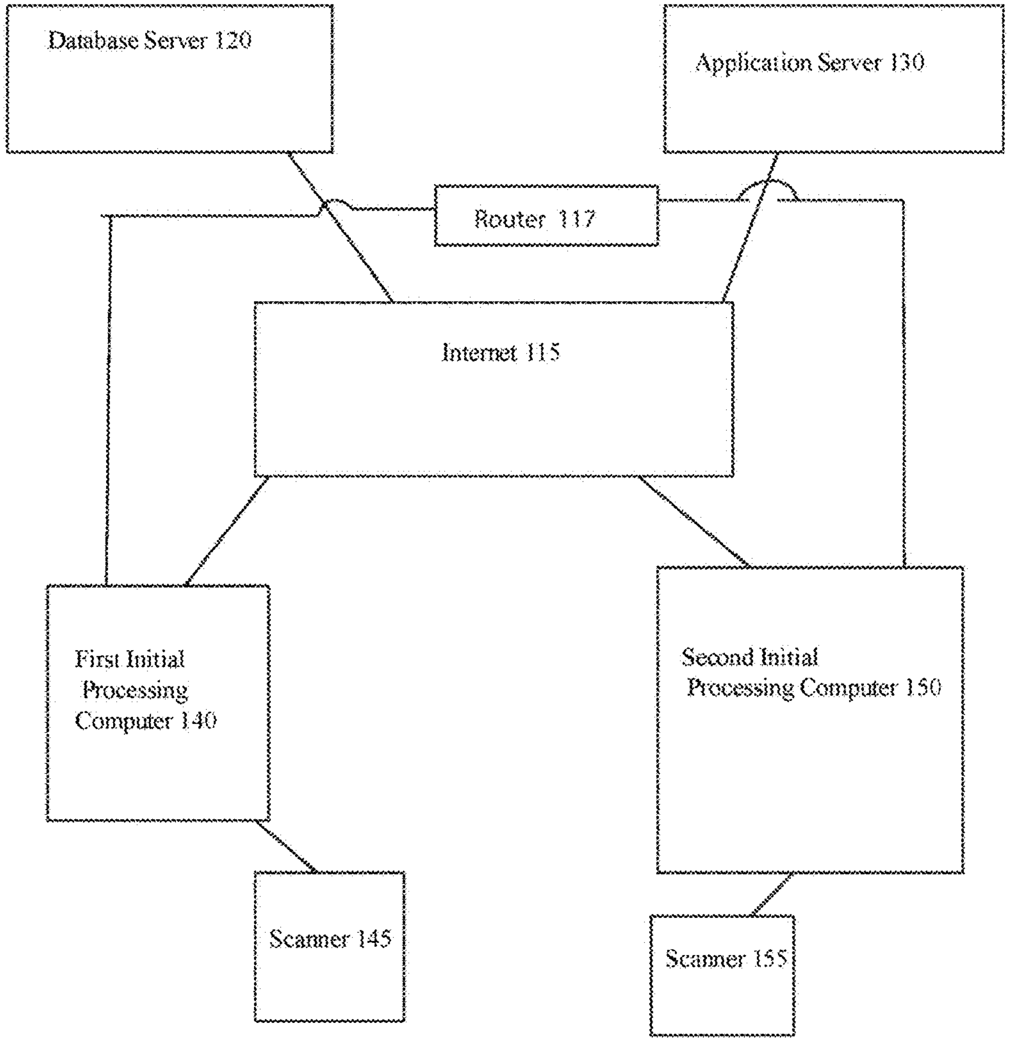
FIG. 10 is a schematic block diagram of the computer network used in any one of the process outlined in FIGS. 1, 3, 5, and 7.

FIG. 10 shows a network layout of a computer network that can be used to carry out the processes shown in FIGS. 1, 3, 5, 7, and 11. For example, there is a computer network which includes a connection through router or through the internet 115. At least one node on this network includes a database server 130. There is also an application server which can be in communication with database server 130 either through the internet 115 or through a router such as a private network. The first initial processing computer and the second initial processing computers are configured to be coupled to associated scanners such as scanner 145 and scanner 155. These scanners are configured to scan through either a CT scan, MRI or other type of scan an ankle joint of an affected leg as well as an ankle joint of a contralateral leg. The information received into these computers can then be transported into the processing computers 140 and/or 150 and then processed and transported over to any one of servers 120 and 130 for further information processing.

While the processing and procedures that can be used for creating a talus implant have been shown above, this type of processing can be used to create other implants as well.

Figure 11:
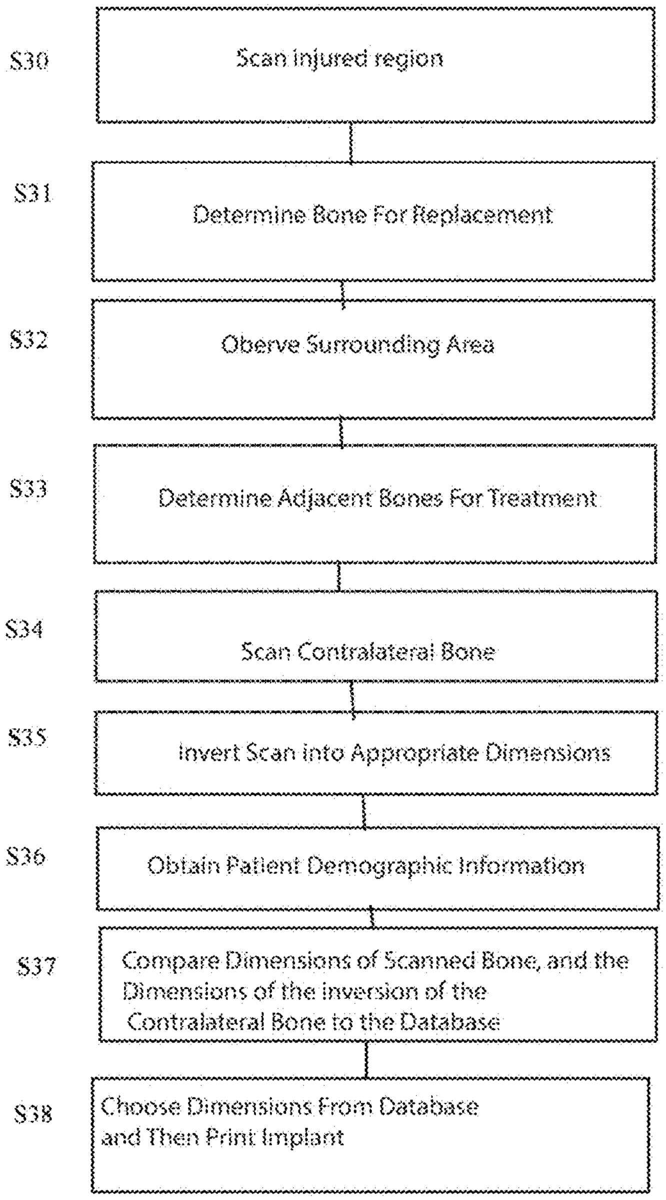
FIG. 11 is a flow chart for the process for printing an implant.

FIG. 11 is a flow chart for the generic process of creating an implant for a joint. For example, an initially injured region is first scanned in step S30. Next, once the region is scanned, the system comprising either a radiologist computer or other physician or medical practitioner can determine which bone(s) primarily need to be replaced in step S31. Next, in step S32 the system/practitioner can scan and/or observe the surrounding area. This step can include either nondestructive evaluation through scanning or through actual incision into the joint and visual observation of the joint if necessary. From this additional scan, the system can determine whether adjacent bones which are adjacent to the primarily damaged bone require any additional treatment such as additional implants, caps or other types of surface treatment. Next, in step S34 the system can scan the contralateral bone/joint. This scan can be for an uninjured body part on an opposite side of the user's body. For example, if a person injures his or her left index finger such as a broken phalange, the process shown in FIG. 11 can be applied. For example, the system would first scan the area of injury to determine if a distal, middle or proximal phalange of the left index finger has been damaged. If for example both the distal and the middle phalange of the left index finger have been essentially crushed and/or shattered requiring an implant, then the system can determine in step S31 that both the distal and the middle phalange need to be replaced. In step S32, the system can observe the surrounding area such as the proximal phalange to determine if a portion of the proximal phalange has been damaged. If an outer or distal tip of the proximal phalange has been damaged, then in step S33 the system can determine that the proximal phalange requires an end treatment requiring a portion of an implant. During this initial scanning phase, the system can obtain dimensions of the damaged bone(s) in the injured region. Next, in step S34 the system can scan the contralateral joint/region which in this instance would be a right index finger, particularly the distal, middle and the proximal phalange of the right index finger. From these scanned dimensions, they can be inverted and compared to the affected or injured region. In many cases if the injured region is so damaged that it cannot offer reliable data, only the inverted dimensions of the contralateral bones/joint will be taken. The patient's demographic information and medical history can also be useful to determine whether there should be any additional modifications to the dimensions are necessary. Next, these dimensions can be compared to a pre-set set of dimensions stored in a database in database server 120. In this case, the length, and diameter of each of the distal, middle and proximal phalanges of a left index finger would be compared to the existing dimensions taken from the inversion of the dimensions of the contralateral affected area. The best match of the dimensions in the database with the inverted dimensions of the contralateral affected are chosen so that these dimensions can be sent to a processing computer 160 and eventually onto a printer such as printer 170 for printing one or more implants.

Thus, this system and process is configured to obtain dimensions of an injured joint, or of the contralateral joint of an injured joint, and then compare these sets of information to information regarding dimensions in a database to determine the best set of dimensions for printing an implant. With greater experience, the database can be populated with many sets of dimensions for different types of patients so that the system can appropriately select the correct set of dimensions for a patient. In addition, the system can provide weighted values of different dimensions to determine which dimension is more indicative of a correct set of dimensions for an implant such as overall length, height, width, and shape. With certain implants length may be more important than height or width. Alternatively, with the case of elongated substantially cylindrical bones such as a phalange, the diameter of a bone may be more important than the length of a bone or vice versa. Furthermore, through pre-set ranges or through previously reported successful implants, the system can determine whether to use the pre-set dimensions of a database or whether to create a new set of dimensions for storage in a database. These new dimensions can be entirely new dimensions which populate a new case for use in the future. For example, if the dimensions of the affected bone or joint area differ by a % amount that is outside of a pre-set range then a new set of dimensions for an implant can be stored in the database rather than having the system rely on an old set of dimensions for use in an implant. This pre-set range can be a difference based upon a pre-set % amount of length, width, height, diameter etc. Some pre-set ranges could be 1%, 0.5%, 2% or any amount of differential up to 3%, 5% or even 10%. Alternatively, the pre-set differences between the measured dimensions and the dimensions that are stored in the database can be based upon a pre-set length, width, height or diameter such as 1 mm, 2 mm or any other type of pre-set dimensions that are set in the system to determine whether there is a suitable match between the measured damaged joint or bone or the inverted dimensions of the contralateral joint or bone and the measurements stored in a database.

Thus, the system is configured to either take a new set of data points for printing an implant or to rely on a library or database of past dimensions for an implant when printing an implant for use in repairing a patient's bone or joint.

Accordingly, while at least one embodiment of the present invention have been shown and described, it is to be understood that many changes and modifications may be made thereunto without departing from the spirit and scope of the invention as defined in the appended claims.

The invention claimed is:

1. A process for printing a talus implant comprising the steps of:

scanning a first ankle joint of a patient comprising a damaged talus and adjacent joints that articulate with the damaged talus, the adjacent joints comprising a subtalar joint, a navicular joint and a tibiotalar joint;

scanning a contralateral ankle joint of the patient comprising a second talus;

obtaining first talus dimensions from the scanned damaged talus;

obtaining second talus dimensions from the scanned second talus of the contralateral joint;

inverting the second talus dimensions to obtain an inverted set of talus dimensions for a talus implant;

comparing the first talus dimensions with a pre-set of dimensions in a database, and determining a first pre-set of talus dimensions for the talus implant based on the comparing;

determining whether there is any arthritis present in the subtalar joint;

determining whether there is any arthritis present in the navicular joint;

determining whether there is any arthritis present in the tibiotalar joint;

based on any arthritis determined to be present in the subtalar joint, the navicular joint and the tibiotalar joint, modifying the first pre-set of talus dimensions or the inverted set of talus dimensions to determine a calculated set of talus dimensions that:

includes a lattice structure configured to encourage interstitial bone growth on a surface of the talus implant; or are compatible with a total ankle replacement system and void of any lattice structure; and exporting the calculated set of talus dimensions to a printer to print the talus implant.

2. The process as in claim 1, wherein modifying the first pre-set of talus dimensions or the inverted set of talus dimensions to determine the calculated set of talus dimensions comprises modifying the inverted set of talus dimensions.

3. The process as in claim 1, wherein modifying the first pre-set of talus dimensions or the inverted set of talus dimensions to determine the calculated set of talus dimensions comprises modifying the first pre-set of talus dimensions.

4. The process as in claim 1, further comprising comparing the demographic information of the patient with the demographic information in the database, and wherein the determining the first pre-set of talus dimensions for the talus implant is based on the comparing the first talus dimensions with the pre-set of dimensions in the database and the comparing the demographic information of the patient with the demographic information in the database.

5. The process as in claim 1, wherein the obtaining the second talus dimensions from the scanned second talus of the contralateral joint comprises obtaining an overall length of the second talus of the contralateral joint.

6. The process as in claim 1, wherein the obtaining the second talus dimensions from the scanned second talus of the contralateral joint comprises obtaining an overall width of the second talus of the contralateral joint.

7. The process as in claim 1, wherein the obtaining the second talus dimensions from the scanned second talus of the contralateral joint comprises obtaining a length of a neck of the second talus of the contralateral joint.

8. The process as in claim 1, wherein the comparing the first talus dimensions of with the pre-set of dimensions in the database comprises comparing at least one of the following dimensions: length of the first talus, width of the first talus, and length of a neck of the first talus.

9. The process as in claim 1, wherein comparing the first talus dimensions with the pre-set of dimensions in the database, and determining the first pre-set of talus dimensions for the talus implant based on the comparing, comprises utilizing a preset tolerance for matching the first talus dimensions with at least one of the pre-set dimensions in said database.

10. The process as in claim 9, wherein said pre-set tolerance comprises a tolerance of a 1% differential.

11. The process as in claim 9, wherein said pre-set tolerance comprises a tolerance of a 5% differential.

12. The process as in claim 1, wherein the determining whether there is any arthritis present in the subtalar joint, the determining whether there is any arthritis present in the navicular joint, and the determining whether there is any arthritis present in the tibiotalar joint comprises determining whether there is any arthritis present in the subtalar joint but not in the navicular joint or the tibiotalar joint.

13. The process as in claim 1, wherein the determining whether there is any arthritis present in the subtalar joint, the determining whether there is any arthritis present in the navicular joint, and the determining whether there is any arthritis present in the tibiotalar joint comprises determining whether there is any arthritis present in the navicular joint but not in the subtalar joint or the tibiotalar joint.

14. The process as in claim 1, wherein the determining whether there is any arthritis present in the subtalar joint, the determining whether there is any arthritis present in the navicular joint, and the determining whether there is any arthritis present in the tibiotalar joint comprises determining whether there is any arthritis present in all of the subtalar joint, the navicular joint and the tibiotalar joint.

15. The process as in claim 1, further comprising determining whether to modify the first set of talus dimensions or the inverted set of talus dimensions based on any arthritis determined to be present in the subtalar joint, the navicular joint and the tibiotalar joint, and wherein the modifying the first pre-set of talus dimensions or the inverted set of talus dimensions to determine a calculated set of talus dimensions is based on the determining whether to modify the first set of talus dimensions or the inverted set of talus dimensions based on any arthritis determined to be present in the subtalar joint, the navicular joint and the tibiotalar joint.

* * * * *